United States Patent [19]

Price et al.

[11] Patent Number: 5,651,976
[45] Date of Patent: Jul. 29, 1997

[54] CONTROLLED RELEASE OF ACTIVE AGENTS USING INORGANIC TUBULES

[75] Inventors: Ronald R. Price, Stevensville; Bruce P. Gaber, Bethesda, both of Md.

[73] Assignee: The United States of America as represented by the Secretary of the Navy, Washington, D.C.

[21] Appl. No.: 509,483

[22] Filed: Jul. 31, 1995

Related U.S. Application Data

[60] Continuation-in-part of Ser. No. 206,149, Mar. 7, 1994, which is a division of Ser. No. 77,503, Jun. 17, 1993, Pat. No. 5,492,696.

[51] Int. Cl.$^6$ ..................... A01N 25/28
[52] U.S. Cl. ............... 424/409; 424/405; 424/417; 424/421; 424/490; 514/963; 427/2.14; 427/213.3; 427/215; 428/402.2; 428/403
[58] Field of Search .................. 424/405, 409, 424/417, 408, 490; 514/563; 427/2.14, 213.3, 215; 428/402.2, 403

[56] References Cited

U.S. PATENT DOCUMENTS

| | | | |
|---|---|---|---|
| 4,017,030 | 4/1977 | Coplan et al. | 239/44 |
| 4,684,524 | 8/1987 | Eckenhoff et al. | 424/469 |
| 5,035,981 | 7/1991 | Runkel et al. | 424/423 |
| 5,049,382 | 9/1991 | Price et al. | 424/450 |
| 5,314,477 | 5/1994 | Brauker et al. | 623/11 |
| 5,326,568 | 7/1994 | Giampapa et al. | 424/426 |

OTHER PUBLICATIONS

Baral et al., "Electroless Metallization of Halloysite, a Hollow Cylindrical 1:1 Aluminosilicate of Submicron Diameter", *Chemistry of Materials* 5 1227-32 (1993).

*Primary Examiner*—Neil S. Levy
*Attorney, Agent, or Firm*—Thomas E. McDonnell; John J. Karasek

[57] ABSTRACT

The present invention is a composition for, and a method of, delivering an active agent at a controlled rate. The composition of the invention is a hollow ceramic or inorganic microtubule, where the active agent is contained within the lumen of the microtubules. Typically, the agent is adsorbed onto an inner surface of the microtubule. The method of the invention is disposing this novel composition in a use environment. In a preferred embodiment of the invention, a microtubule is a tubule having an inner diameter of less than 0.2 µm, and microtubules are tubules having an average inner diameter less than 0.2 µm. In a preferred embodiment, the hollow ceramic or inorganic microtubule is a mineral microtubule, such as halloysite, cylindrite, boulangerite, or imogolite. In a more preferred embodiment of the invention, the mineral microtubule has a biodegradable polymeric carrier disposed in its lumen. In a preferred embodiment of the invention, the inner diameter of the microtubules varies from about 0.20 µm to about 0.35 µm, or averages about 0.40 µm. In another preferred embodiment, of the invention, the inner diameter of the microtubules varies from about 200 Å to about 1000 Å.

12 Claims, No Drawings

CONTROLLED RELEASE OF ACTIVE AGENTS USING INORGANIC TUBULES

CROSS-REFERENCE TO RELATED APPLICATIONS

This application is a continuation-in-part of co-pending U.S. patent application Ser. No. 8 08/206,149 pending filed Mar. 7, 1994, by Ronald R. Price et al., which was a divisional of U.S. patent application Ser. No. 08/077,503, filed Jun. 17, 1993 U.S. Pat. No. 5,492,696 by Ronald R. Price et al. Both applications are incorporated herein by reference in their entireties for all purposes.

BACKGROUND OF THE INVENTION

1. Field of the Invention

This invention relates to compositions and methods for releasing active agents at a selected rate. More particularly, this invention relates to such methods and compositions using inorganic microtubular ceramics, and especially naturally occurring microtubular minerals for environmentally friendly controlled release.

2. Description of the Related Art

Active agents are chemicals that have some effect in some environment of use. For almost any active agent, for use in almost any use environment, it is desired to modulate the release of the active agent into the use environment, so that the active agent is released into the use environment at a selected rate, and over a selected time. There are several, frequently complementary, reasons for modulating active agent release.

Many active agents are preferably released at a desired concentration, or in a desired concentration range. Drugs, for example, are preferably introduced into the body within a therapeutic range. Below this range, there will not be enough of the drug in the body to achieve the desired therapeutic effect. Above this range, no additional therapeutic effect will be conferred, or adverse side effects of the drug will outweigh the therapeutic effect of the drug.

Analogous dynamics are at work for most every active agent. As another example, antifouling agents for use on ship hulls are typically environmentally unfriendly. Thus, it is desired to control the release rate of these antifouling agents, to keep their release into the environment at an acceptable level. At the same time, it is desired to release these antifouling agents at effective levels. See generally U.S. Pat. No. 5,049,382, issued Sep. 17, 1991 to Price et al.

Likewise, many active agents are preferably released at a sustained rate over a desirable period. For example, many drugs (e.g., antibiotics) are preferably absorbed and metabolized by the body over a prolonged therapeutic course of treatment. Traditionally, this is done by administering repeated, regular doses (e.g., regular oral or injected doses), or by a sustained administration, such as an intravenous drip. Other drugs (e.g., antihypertensive drugs, birth control hormones) do not have a finite course of treatment. For these drugs, sustained controlled delivery is a matter of convenience and an assurance against a lapse of memory.

Sustained delivery is also desired for many other active agents. For antifouling agents, it is highly desirable to sustain delivery of an effective amount of the antifouling agent for as long as possible, to maximize the time between applications of the agent. For pesticides, pheromones, and other active agents used to control pest populations, sustained delivery of these agents for at least the duration of a growth or reproduction cycle is highly desirable. See generally U.S. Pat. No. 4,017,303, issued April 12, 1977 to Coplan et al.

For these and other types of active agents, several concerns present themselves. It is generally desirable to release an active agent at a controlled rate, to maintain a constant level of the active agent. Unfortunately, many of the systems used for the modulated delivery of active agents do not release these active agents at a controlled rate. Systems using layered structures that ablade or dissolve one layer at a time tend to release their active agents in cycles, with the levels of active agents oscillating between highs and lows.

Liposomal tubules and other microstructures, which have been proposed for use in a system for the modulated delivery of an active agent, (see Price et al., supra) have several shortcomings. These tubules must be manufactured: they do not occur naturally. They release their entrapped contents very quickly, over a time scale of minutes. They do not inherently permit a low solubility active agent to be readily introduced into a use environment, at a desired effective rate, such as effectively delivering a hydrophobic active agent in vivo. However, liposome tubules do have several advantages: they are small enough to be injected or to be incorporated in a coating such as an antifouling paint, and they have broad applicability to a range of active agents and use environments.

Metal tubules and other microstructures have also been proposed for use in the modulated release of an active agent. These metal structures typically are made by metallizing a lipid microstructure. In addition to the additional processing and cost concerns inherent to metallized tubules, there is the additional environmental unfriendliness associated with many metals used in these applications (e.g., copper).

Polymers and other carriers are sometimes used for the modulated release of an active agent that has at least some solubility in these carriers. In these applications, the active agent is mixed with the carrier, to dissolve the active agent in the carrier. As the active agent diffuses through the carrier to the interface of the carrier and the use environment, the active agent is released into the use environment. Typical examples of such systems are flea and tick collars for pets. Unfortunately, many active agents have undesirably low solubility in many of the available carriers. A consequence of this low solubility is that in many instances, the delivery system will contain only an undesirably small amount of the active agent, limiting the useful life of the delivery system. For example, flea and tick collars for pets have undesirably short useful lives, shorter than the flea and tick seasons in many parts of the country. A delivery system that would permit the inclusion of a larger volume of active agent in a delivery system is desired. Also, many of these polymers used in modulated release applications are environmentally unfriendly.

SUMMARY OF THE INVENTION

Accordingly, it is an object of this invention to provide an improved structure and method for the controlled release of active agents, including drugs (including antibiotics), antifouling agents, biocides, pesticides, herbicides, molluskicides, pheromones and other scents, etc.

It is a further object of this invention to provide a structure and method for the controlled release of an active agent over a time scale of days, months, or years.

It is a further object of this invention to provide a structure and method for the controlled release of an active agent where all the components of the delivery system are environmentally friendly, thus making the system as a whole environmentally friendly.

It is a further object of this invention to provide a structure and method for the controlled release of an active agent using naturally occurring microtubules.

It is a further object of this invention to provide a broadly-applicable, low-cost structure and method for the controlled release of an active agent.

It is a further object of this invention to provide a structure and method for the controlled release of a low solubility active agent into a use environment at a desirable effective rate.

These and additional objects of the invention are accomplished by the structures and processes hereinafter described.

The present invention is a composition for, and a method of, delivering an active agent at a controlled rate. The composition of the invention is a hollow ceramic or inorganic microtubule, where the active agent is contained within the lumen of the microtubules. Typically, the agent is adsorbed onto an inner surface of the microtubule. The method of the invention is disposing this novel composition in a use environment. In a preferred embodiment of the invention, a microtubule is a tubule having an inner diameter of less than 0.2 µm, and microtubules are tubules having an average inner diameter less than 0.2 µm. In a preferred embodiment, the hollow ceramic or inorganic microtubule is a mineral microtubule, such as halloysite, cylindrite, boulangerite, or imogolite. In a more preferred embodiment of the invention, the mineral microtubule has a biodegradable polymeric carrier disposed in its lumen. In a preferred embodiment of the invention, the inner diameter of the microtubules varies from about 0.20 µm to about 0.35 µm, or averages about 0.40 µm. In another preferred embodiment, of the invention, the inner diameter of the microtubules varies from about 200 Å to about 1000 Å.

DETAILED DESCRIPTION OF THE PREFERRED EMBODIMENTS

A. Adsorption/Desorption Processes

Chemical agents, including the active agents of interest to the present invention, can enter or exit from the internal volume (lumen) of a cylindrical tubule by several mechanisms. For example, active agents can enter or exit tubules by capillary action, if the tubules are sufficiently wide. Capillary attraction and release occurs in tubules having inner diameters of at least about 0.2 µm. Capillary attraction is relatively weak: agents in tubules having inner diameters of at least about 10 µm, typically will be released in a matter of hours, without the use of other barriers to release.

In contrast to capillary action, adsorption/desorption processes occur over much smaller distance scales, typically on the order of about 1000 Å. Thus, for tubules in this size range, adsorption/desorption is the controlling process for the release of an active agent inside the interior volume of a microtubule. For a molecule of an active agent contained within the interior volume of a microtubule to reach the end of the tubule, so that the molecule can be released into the environment, the molecule must diffuse through the interior of the tubule while repeatedly being adsorbed and then desorbed by the inner surface of the tubule. This process, which may be conceptualized as a chromatography type of process, is much slower than capillary action, by several orders of magnitude.

B. Mineral Microstructures

Several naturally occurring minerals will, under appropriate hydration conditions, form tubules and other microstructures suitable for use in the present invention. The most common of these is halloysite, an inorganic aluminosilicate belonging to the kaolinite group of clay minerals. See generally, Bates et al., "Morphology and structure of endellite and halloysite", *American Minerologists* 35 463–85 (1950), which remains the definitive paper on halloysite. The mineral has the chemical formula $Al_2O_3 \cdot 2SiO_2 \cdot nH_2O$. In hydrated form the mineral forms good tubules. In dehydrated form the mineral forms broken, collapsed, split, or partially unrolled tubules.

The nomenclature for this mineral is not uniform. In the United States, the hydrated tubule form of the mineral is called endellite, and the dehydrated form is called halloysite. In Europe, the hydrated tubule form of the mineral is called halloysite, and the dehydrated form is called meta-halloysite. To avoid confusion, mineralogists will frequently refer to the hydrated mineral as halloysite 10 Å, and the dehydrated mineral as halloysite 7 Å.

Bates et al. present data on the tubes, which is summarized below:

|  | Range (Å) | Median (Å) |
|---|---|---|
| Tube diameter: | 400–1900 | 700 |
| Hole diameter: | 200–1000 | 400 |
| Wall thickness: | 100–700 | 200 |

Tube lengths range from 0.1 to about 0.75 µm. Morphologically, both hydrated and dehydrated halloysite comprise layers of single silica tetrahedral and alumina octahedral units. They differ in the presence or absence of a layer of water molecules between the silicate and alumina layers. The basal spacing of the dehydrated form is about 7.2 Å, and the basal spacing of the hydrated form is about 10.1 Å (hence the names halloysite 7 Å and halloysite 10 Å). The difference, about 2.9 Å, is about the thickness of a monolayer of water molecules.

A theory for the formation of hollow tubular microcrystals is presented in Bates et al. Water molecules interposed between the gibbsite ($Al_2O_3$) and silicate ($SiO_2$) layers results in a mismatch between the layers, which is compensated by curvature of the layers.

Halloysite 10 Å dehydrates to halloysite 7 Å at about 110° C. All structural water is lost at about 575° C. The interlayer water in halloysite 10 Å may be replaced by organic liquids such as ethylene glycol, di- and triethylene glycol, and glycerine.

Another mineral that will, under appropriate hydration conditions, form tubules and other microstructures is imogolite.

Another mineral that will, under appropriate conditions, form tubules and other microstructures is cylindrite. Cylindrite belongs to the class of minerals known as sulfosalts.

Yet another mineral that will, under appropriate conditions, form tubules and other microstructures is boulangerite. Boulangerite also belongs to the class of minerals known as sulfosalts.

C. Embodiments of the Invention

In preferred embodiments of the invention, an active agent is adsorbed onto the inner surface of the lumen of a mineral microstructure. Skilled practitioners will be able to employ known techniques for introducing a wide range of active agents into the lumen of a mineral microstructure according to the invention, thereby making a structure for the modulated release of the active agent. Such structures according to the invention may be used as-is, i.e., as free structures which may be dispensed as desired. Dispensing techniques include scattering, spreading, injecting, etc.

An important aspect of the microstructures is the size of the lumen. Preferred inner diameters range from about 200

Å to about 2000 Å Preferred lengths range from about 0.1 μm. to about 2.0 μm. Lumen size selection is governed in part by the availability of ceramic or inorganic microstructures within the suitable size range. Lumen size selection is also governed by the choice of active agent, and the choice of any carrier, coating, or matrix (see infra). The physical and chemical properties (e.g., viscosity, solubility, reactivity, resistance to wear, etc.) of the active agent, any carrier, any coating and any matrix will be considered by a skilled practitioner. Lumen size selection is also governed by the desired release profile for the active agent.

Such structures may be included in a surrounding matrix, such as a paint or a polymer. After release from the mineral microstructures, the active agent then diffuses through the surrounding matrix to interface with the use environment. If the surrounding matrix is ablative in the use environment, then the diffusion distance through the matrix is mitigated or eliminated by this ablation.

Suitable surrounding matrices will typically be insoluble in the use environment. These matrices include paints (including marine paints), stains, lacquers, shellacs, wood treatment products, and all manner of applied coatings.

In another embodiment of the invention, the lumen of the microstructure contains both an active agent and a carrier. This carrier further modulates the release of the active agent from the lumen of the microstructure. The active agent may be soluble or mobile in the carrier. In this case, the release rate of the active agent will depend on the solubility and diffusion rate of the active agent through the carrier and any coating or matrix. The active agent may be insoluble or immobile in the carrier. In this case, the release rate of the active agent will depend on the release rate of the carrier from the tubule, and any coating or matrix.

In another embodiment of the invention, the microstructure is coated with a coating material. This coating further modulates the release of the active agent from the lumen of the microstructure. By carefully selecting a coating for its chemical and physical properties, very precise control of the release of the active agent from the lumen of the microstructure can be achieved.

For example, a thermoset polymer may be used as a coating in a preferred embodiment of the invention. By carefully selecting the degree of crosslinking in a thermoset polymer coating, and thus the porosity of the thermoset polymer coating, one can obtain a precise degree of control over the release of the active agent from the lumen of the microstructure. Highly crosslinked thermoset coatings will retard the release of the active agent from the lumen more effectively than less crosslinked thermoset coatings.

Likewise, the chemical properties of a coating may be used to modulate the release of an active agent from the lumen of a microstructure. For example, it may be desired to use a hydrophobic active agent in an aqueous use environment. However, if one were to load a highly hydrophobic active agent into the lumen of a microstructure according to the invention, and then place this loaded microstructure in an aqueous use environment, the active agent typically would release into the use environment unacceptably slowly, if at all.

This problem of active agents that are highly insoluble in an intended use environment is a common one. Many antibiotics are highly insoluble in the serum. This problem can be largely mitigated by coating the microstructures with a coating material in which the active agent has an intermediate solubility (i.e., a solubility somewhere between the solubility of the active agent in itself and the solubility of the active agent in the use environment).

D. Active Agents

A wide range of active agents will be suitable for use in the present invention. These suitable active agents include pesticides, antibiotics, antihelmetics, antifouling compounds, dyes, enzymes, peptides, bacterial spores, fungi, hormones, etc.

Suitable herbicides include tri-chloro compounds (triox, ergerol), isothiazoline, and chlorothanolil (tufficide). Suitable pesticides include malathion, spectricide, and rotenone. Suitable antibiotics include albacilin, amforol, amoxicillin, ampicillin, amprol, ariaprime, aureomycin, aziumycin, chloratetracycline, oxytetracycline, gallimycin, fulvicin, garacin, gentocin, liquamicin, lincomix, nitrofurizone, penicillin, sulfamethazine, sulfapyridine, fulfaquinoxaline, fulfathiozole, and sulkamycin. Suitable antihelmetics include ivermictin, vetisulid, trichorofon, tribrissen, tramisol, topazone, telmin, furox, dichlorovos, anthecide, anaprime, acepromazine, pyrantel tartrate, trichlofon, fanbentel, benzimidazoles, and oxibenzidole. Suitable antifouling agents include ergerol, triazine, decanolactone, angelicalactone, galactilone, any lactone compound, capsicum oil, copper sulphate, isothiazalone, organochlorine compounds, organotin compounds, tetracyclines, calcium ionophores such as 504, C23187, tetracycline. Suitable hormones include estrogen, progestin, testosterone, and human growth factor.

E. Carriers

Carriers are selected in view of their viscosity and the solubility of the active agent in the carrier. The carrier typically should possess a sufficiently low viscosity to fill the lumen of the microstructure. Alternatively, a low viscosity carrier precursor may be used, and the carrier formed in situ. For example, the lumen may be filled with a low viscosity monomer, and this monomer subsequently may be polymerized inside the lumen. Accordingly, suitable carriers include low molecular weight polymers and monomers, such as polysaccharides, polyesters, polyamides, nylons, polypeptides, polyurethanes, polyethylenes, polypropylenes, polyvinylchlorides, polystyrenes, polyphenols, polyvinyl pyrollidone, polyvinyl alcohol, ethyl cellulose, gar gum, polyvinyl formal resin, water soluble epoxy resins, quietol 651/nma/ddsa, aquon/ddsa/nsa, urea-formaldehyde, polylysine, chitosan, and polyvinylacetate and copolymers and blends thereof.

Frequently, skilled practitioners may desire to select a carrier that has a very highly selective binding affinity for an active agent of interest. A carrier that has a highly selective binding affinity for an active agent will tend to release that active agent very slowly. Thus, very slow release rates may be achieved by the use of carriers with high binding affinities for the active agent to be released. Skilled practitioners will recognize that a consequence of the extensive research that has been done on surface acoustic wave (SAW) analysis is that a large number of polymers have been identified as selective adsorbents for particular organic analytes. See generally, D. S. Ballantine, Jr., S. L. Rose, J. W. Grate, H. Wohltjen, *Analytical Chemistry* 58 3058–66 (1986), and references therein, incorporated by reference herein. See also R. A. McGill et al., "Choosing Polymer Coatings for Chemical Sensors", CHEMTECH 24 (9) 27–37, and references therein, incorporated by reference herein.

Preferred carriers include polylactate, polyglycolic acid, polysaccharides (e.g., alginate or chitosan), and mixtures thereof. Each of these carriers is biodegradable. When used in combination with a naturally occurring mineral microtubule, such biodegradable carriers provide an environmentally friendly delivery system.

F. Examples

Having described the invention, the following examples are given to illustrate specific applications of the invention, including the best mode now known to perform the invention. These specific examples are not intended to limit the scope of the invention described in this application.

EXAMPLE 1:

Preparation of Environmentally Friendly Microtubules, and Measurement of Release Rate Therefrom Preparation of halloysite microcylinders The halloysite was obtained as a crude sample of the lump clay deposit and was hydrated in distilled water, containing 5% by weight sodium metaphosphate. The clay was then crudely crushed by hand, using a metal hammer to break up the large lumps, and foreign material and rocks were sorted by hand. The sample was then transferred into a common kitchen blender adding 200 g of the sample to 1 liter of water. The mixture was allowed to agitate at a medium speed for a period of 30 minutes. The material in suspension was removed and fresh water containing 5% by weight Na metaphosphate was added and the process repeated until the clumps would no longer break down. Following this step the suspension was allowed to stand in a 3 L graduate cylinder for 10 minutes, and then the suspended portion of the sample was removed for further processing. The gravity settlement allowed further separation of quartz sand particles from the halloysite. The resultant suspension was spun in an IEC Model C-6000 centrifuge in 1 L bottles and the supernatant removed and replaced with fresh distilled water, and the process was repeated an additional two cycles. The resultant slurry was then filtered through a cloth paint filter cone to remove any remaining large clumps, which were then ground in a mortar and pestle and retreated as before. Once the halloysite sample was found to be substantially free of foreign material, it was spun out of the water suspension and allowed to air dry. This yielded a white cake of halloysite that was then powdered in a mortar and pestle, to yield a friable white powder.

Method of entrapment

The powder of dry halloysite microcylinders were treated by the following scheme. The active agent which is to be employed by the first method of entrapment should be a solid at or below 40° C. In this method both the halloysite and the agent are heated to a temperature just above the melting point of the agent. The best method should be a vacuum oven, if possible, under a partial vacuum to aid in removal of retained gasses within the core of the microcylinders.

The halloysite was observed to be "wet" with the active agent. Following this step the vacuum was released and the resultant agent/microcylinders complex was suspended in a dispersant that was not a solvent for the agent, and was at the same temperature as the agent/halloysite. With sufficient agitation, the temperature was lowered until the agent became a solid again. The agitation optionally may be stopped at this point and the suspension allowed to settle. The dispersant was removed and the resultant halloysite/ agent complex was then suspended in a solvent for the agent. This resulted in the removal of the exogenous agent from the microcylinder.

The second method employed utilized a suspension of the halloysite and agent in solution of a suitable biodegradable polymer such as a poly-lactic/polyglycolic acid system, which was diluted in a suitable solvent such as methanol. The resultant suspension was then injected into a fluidized bed to flash off the solvent and yield a halloysite/agent mixture which had an outer coating of an environmentally benign coating of degradable polymer.

The third method required the active agent to be miscible with the polylactic/polyglycolic acid mixture, or that the active agent be very small particulates (nanoparticulates). This mixture was then entrapped in the central core of the microcylinders by a method similar to that in the original method, except that the agent was allowed to flash off in the vacuum at ambient temperatures.

Assay for Microencapsulation

To determine the encapsulation efficiency, the microcylinders were crushed and suspended in a suitable solvent. The suspension was agitated for several hours to ensure full dissolution of the active agent. The determination of concentration of active agents was made either by weight or by suitable chemical analysis.

Laboratory Determination of Release Rate

The microtubules were added to a conical 50 ml disposable centrifuge, and 50 ml of deionized $H_2O$ was added. Concentration determinations were made based on absorption in a Perkin Elmer UV/Vis series 6000 spectrophotometer. A peristaltic pump was employed to pump the solution through a quartz flow cell where absorption measurements were made each half-hour. When necessary, the deionized $H_2O$ was changed to prevent saturation.

Additional modification of the release characteristics has been achieved through employment of a further layer of the degradable polymeric material, where the secondary layer was free of any active agent. This provides a barrier coating to protect against short term exposure to the entrapped agent during handling. This coating then degrades in the environment at a rate that is determinable by the degree of cross-linking of the co-polymers or by employment of an additional crosslinking agent. This allows for a delayed release product. By mixing the thickness of the overcoating, the delay has been tailored to initiate release over a considerable time period.

For shorter term release profiles (<300 hr) polysaccharides (including alginate and chitosan) have provided a carrier and a coating that was biodegradable. Due to the open nature of the gel, the release rate has been rather fast, depending on the agent.

Obviously, many modifications and variations of the present invention are possible in light of the above teachings. It is therefore to be understood that, within the scope of the appended claims, the invention may be practiced otherwise than as specifically described.

What is claimed is:

1. A composition for use in the delivery of an active agent at an effective rate for a selected time, comprising:
    hollow mineral microtubules selected from the group consisting of halloysite, cylindrite, boulangerite, and imogolite, wherein said microtubules have inner diameters ranging from about 200 Å to about 2000 Å, and have lengths ranging from about 0.1 µm to about 2.0 µm, wherein said active agent is selected from the group consisting of pesticides, antibiotics, antihelmetics, antifouling compounds, dyes, enzymes, peptides, bacterial spores, fungi, hormones, and drugs and is contained within the lumen of said microtubules, and wherein outer and end surfaces of said microtubules are essentially free of said adsorbed active agent.

2. The composition of claim 1, wherein said active agent is adsorbed onto an inner surface of said microtubules.

3. The composition of claim 1, wherein said composition further comprises a diffusion modulation component disposed inside the internal volume of said microtubules, for retarding the release of said active agent from said microtubules at a selected rate.

4. The composition of claim 3, wherein said diffusion modulation component is a polymer selected to provide said active agent with a selected diffusivity through said polymer.

5. The composition of claim 4, wherein said polymer has a selected porosity.

6. The composition of claim 4, wherein said polymer has a selected binding affinity for said active agent.

7. The composition of claim 4, wherein said polymer is a biodegradable polymer.

8. The composition of claim 4, wherein said polymer selectively binds to said active agent.

9. The composition of claim 1, wherein said microtubules have an adherent barrier coating for retarding the release of said active agent from said microtubules to a selected rate.

10. The composition of claim 9, wherein said barrier coating is a polymer coating having a selected porosity.

11. A composition for use in the delivery of an active agent, at an effective rate for a selected time, into a fluid use environment wherein said active agent has a limited solubility, comprising:

hollow cylindrical mineral microtubules selected from the group consisting of halloysite, cylindrite, boulangerite, and imogolite, wherein said microtubules have inner diameters ranging from about 200 Å to about 2000 Å, and have lengths ranging from about 0.1 μm to about 2.0 μm, wherein said active agent is selected from the group consisting of pesticides, antibiotics, antihelmetics, antifouling compounds, dyes, enzymes, peptides, bacterial spores, fungi, hormones, and drugs and is adsorbed onto an inner surface of said microtubules, wherein said microtubules are adherently coated with a coating, wherein said coating is wettable by said fluid and by said active agent, and wherein said coating is permeable to said active agent.

12. The composition of claim 1, wherein said microtubules have inner diameters ranging from about 200 Å to about 1000 Å, and have lengths ranging from about 0.1 μm to about 0.75 μm.

* * * * *